US011179446B2

(12) United States Patent
Rehan et al.

(10) Patent No.: US 11,179,446 B2
(45) Date of Patent: Nov. 23, 2021

(54) COMPOSITIONS AND METHOD FOR ADMINISTERING PPARGAMMA AGONISTS, SURFACTANT PEPTIDES AND PHOSOPHOLIPIDS

(71) Applicant: LUNDQUIST INSTITUTE FOR BIOMEDICAL INNOVATION AT HARBOR—UCLA MEDICAL CENTER, Torrance, CA (US)

(72) Inventors: Virender K. Rehan, Torrance, CA (US); John S. Torday, Torrance, CA (US); Frans J. Walther, Torrance, CA (US); Alan J. Waring, Torrance, CA (US); Larry M. Gordon, Torrance, CA (US)

(73) Assignee: LUNDQUIST INSTITUTE FOR BIOMEDICAL INNOVATION AT HARBOR—UCLA MEDICAL CENTER, Torrance, CA (US)

( * ) Notice: Subject to any disclaimer, the term of this patent is extended or adjusted under 35 U.S.C. 154(b) by 345 days.

(21) Appl. No.: 16/082,224

(22) PCT Filed: Mar. 6, 2017

(86) PCT No.: PCT/US2017/020881
§ 371 (c)(1),
(2) Date: Sep. 4, 2018

(87) PCT Pub. No.: WO2017/155857
PCT Pub. Date: Sep. 14, 2017

(65) Prior Publication Data
US 2020/0289626 A1 Sep. 17, 2020

Related U.S. Application Data

(60) Provisional application No. 62/304,845, filed on Mar. 7, 2016.

(51) Int. Cl.
| A61K 47/24 | (2006.01) |
| A61K 38/17 | (2006.01) |
| A61P 11/00 | (2006.01) |
| A61K 9/00 | (2006.01) |
| A61K 31/4439 | (2006.01) |

(52) U.S. Cl.
CPC .......... *A61K 38/395* (2013.01); *A61K 9/0078* (2013.01); *A61K 31/4439* (2013.01); *A61K 47/24* (2013.01); *A61P 11/00* (2018.01)

(58) Field of Classification Search
CPC .............. A61K 38/395; A61K 31/4439; A61K 9/0078; A61K 47/24; A61P 11/00
See application file for complete search history.

(56) References Cited

U.S. PATENT DOCUMENTS

| 9,238,058 B2 | 1/2016 | Johansson et al. |
| 9,815,869 B2 | 11/2017 | Notter et al. |
| 10,717,777 B2 | 7/2020 | Walther et al. |
| 2010/0055164 A1* | 3/2010 | Notter ............. C07F 9/4075 424/450 |
| 2011/0003733 A1* | 1/2011 | Pivetti ............ A61K 9/0082 514/1.5 |
| 2014/0044775 A1 | 2/2014 | Notter et al. |
| 2015/0125515 A1* | 5/2015 | Notter ............. C07K 7/08 424/450 |

FOREIGN PATENT DOCUMENTS

| EP | 2644619 A1 * | 10/2013 | ....... C07K 14/43518 |
| EP | 2644619 A1 | 10/2013 | |
| WO | 03092685 A1 | 11/2003 | |
| WO | 2008011559 A2 | 1/2008 | |
| WO | 2008044109 A1 | 4/2008 | |
| WO | 2011115538 A1 | 9/2011 | |
| WO | 2013120058 A2 | 8/2013 | |

OTHER PUBLICATIONS

Schachtrup et al (Biochimica et Biophysica Acta, 2008, 1781, 314-320) (Year: 2008).*
Kimura et al (Nephrol Dial Transplant, 2008, 23:2496-2503) (Year: 2008).*
Johansson et al (J Appl Physiol, 2003, 95, 2055-2069) (Year: 2003).*
Whitsett et al (Physiological Reviews, vol. 75, No. 4, Oct. 1995) (Year: 1995).*
Waldrep et al (Current Drug Delivery, 2008, 5, 114-119) (Year: 2008).*
Cavender et al., "Therapeutic Potential of Aleglitazar, a New Dual PPAR-alpha/gamma Agonist", American Journal of Cardiovascular Drugs, 2010, vol. 10, No. 4, pp. 209-216.
Dasgupta et al., "Hyperoxia-induced Neonatal Rat Lung Injury Involves Activation of TGF-beta and Wnt Signaling and is Protected by Rosiglitazone", Am J Phsyiol Lung Cell Mol Physiol., Jun. 2009, pp. 1-11, Retrieved from the Internet: URL:https://www/ncbi.nlm.nih.gov/pmc/articles/PMC3286237/?report=printable, retrieved on Jul. 20, 2020.
Extended European Search Report for EP Application No. 17763818.6, dated Oct. 9, 2020, 10 pages.
International Search Report and Written Opinion for PCT/US2017/020881 dated Aug. 15, 2017, 19 pages.
(Continued)

*Primary Examiner* — Sudhakar Katakam
(74) *Attorney, Agent, or Firm* — Sheppard Mullin Richter & Hampton LLP

(57) ABSTRACT

The present disclosure provides compositions and therapies that can address both the symptoms and disorders associated with insufficient surfactant production and hyperoxia. In one embodiment, the composition can be formulated for aerosol delivery during ventilation therapy. The composition can comprise one or more of the following: a PPAR gamma agonist, a surfactant peptide, and one or more phospholipids. The compositions are formulated to provide the complementary benefits of reducing the likelihood of developing or the severity of RDS in infants, as well as protecting and promoting lung maturation in a hyperoxic environment.

18 Claims, 7 Drawing Sheets

Specification includes a Sequence Listing.

(56) References Cited

OTHER PUBLICATIONS

International Search Report and Written Opinion of PCT/US2016/067317 dated Apr. 13, 2017 (9 pages).
Kim et al., "Ursolic Acid, a Potential PPARgamma Agonist, Suppresses Ovalbumin-Induced Airway Inflammation and Penh by Down-Regulating IL-5, IL-13 and IL-17 in a Mouse Model of Allergic Asthma", European Journal of Pharmacology, 2013, vol. 701, No. 1, pp. 131-143.
Morales et al., "Nebulized PPAR gamma agonists: A Novel Approach to Augment Neonatal Lung Maturation and Injury Repair in Rats", Pediatric Research, vol. 75, No. 5, Jan. 2014, pp. 631-640.
Sahagun et al., Modulation of PPAR-gamma by Nutraceutics as Complementary Treatment for Obesity-Related Disorders and Inflammatory Diseases, PPAR Research, 2012, vol. 2012, No. 318613, pp. 1-18.
Silva et al., "Recent Advances in the Mechanisms of Lung Alveolarization and the Pathogenesis of Bronchopulmonary Dysplasia", American Journal of Physiology—Lung Cellular and Molecular Physiology, vol. 309, No. 11, Dec. 2015, p. L1239-L1272.
Xie et al., "L312, a Novel PPARgamma Ligand with Potent Anti-Diabetic Activity by Selective Regulation", Biochimica et Biophysica Acta, Oct. 2014, vol. 1850, No. 1, pp. 62-72, DOI: 10.1016/j.bbagen.2014.09.027.

\* cited by examiner

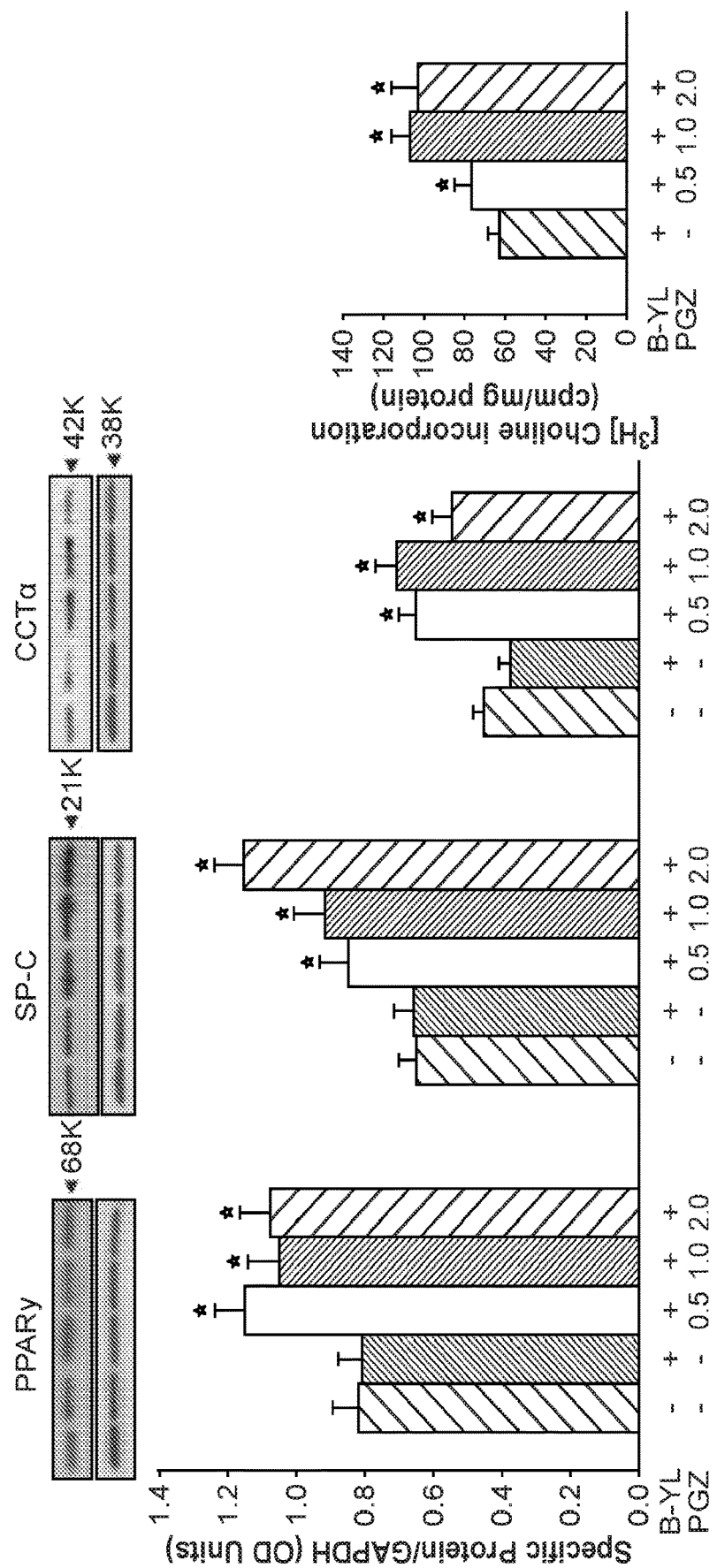

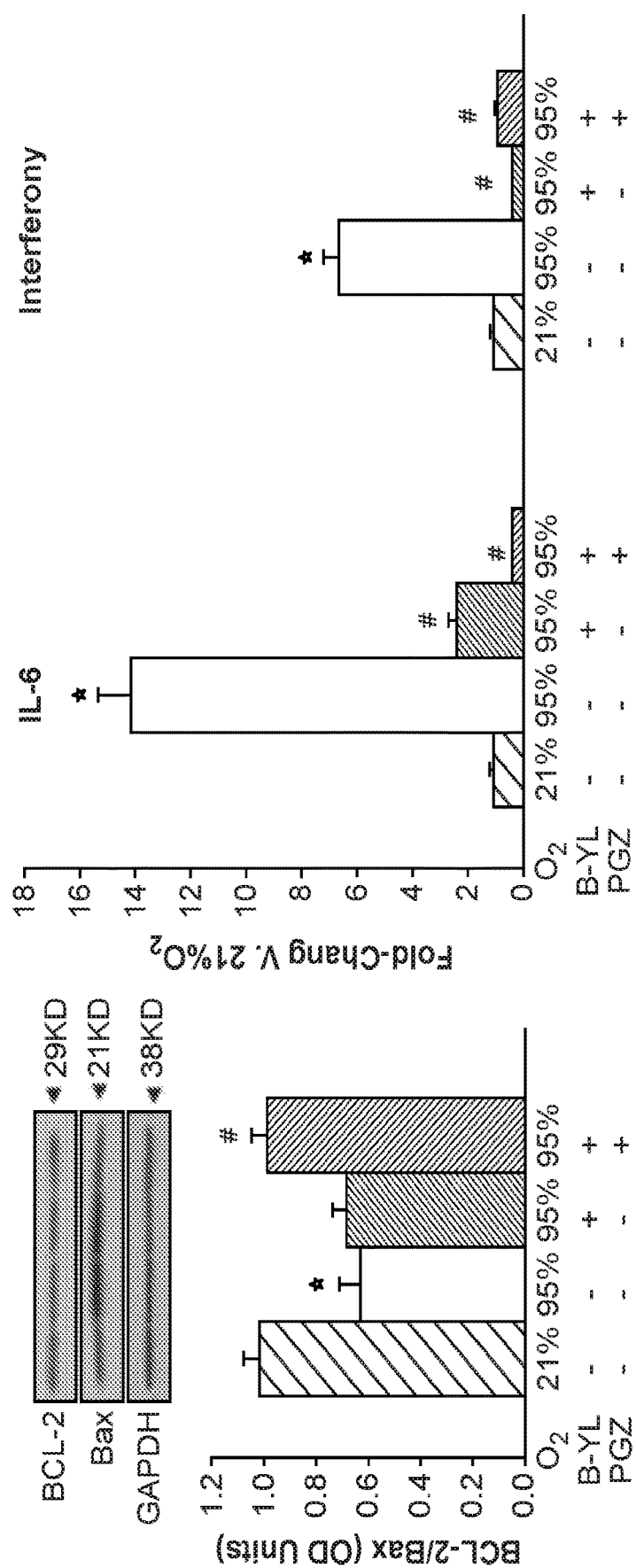

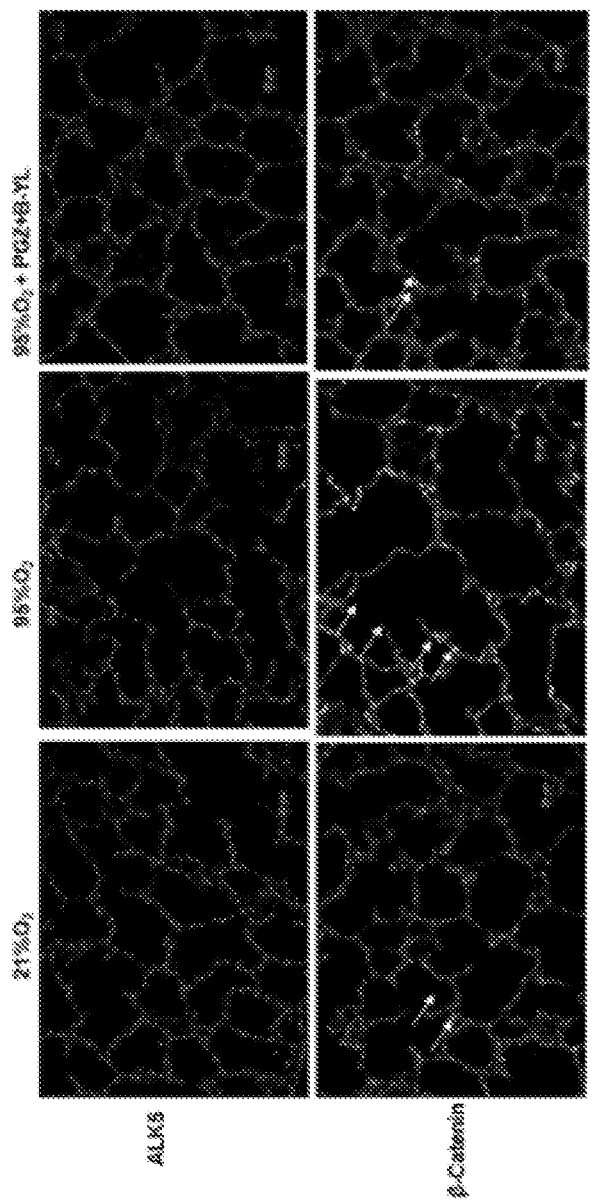

SEQUENCE LISTING

```
<160> NUMBER OF SEQ ID NOS: 26

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 1

Xaa Trp Leu Tyr Arg Ala Leu Ile Lys Arg Ile Gln Ala Xaa Ile
1               5                   10                  15

<210> SEQ ID NO 2
```

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (14)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 2

Arg Xaa Leu Pro Gln Leu Val Tyr Arg Leu Val Leu Arg Xaa Ser
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Lys Gly Gly
1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Ala Thr Lys
1

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Phe Pro Ile Pro Leu Pro Tyr
1               5

<210> SEQ ID NO 6
<211> LENGTH: 78
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Phe Pro Ile Pro Leu Pro Tyr Cys Trp Leu Cys Arg Ala Leu Ile Lys
1               5                   10                  15
```

```
Arg Ile Gln Ala Met Ile Pro Lys Gly Ala Leu Ala Val Ala Val Ala
                20                  25                  30

Gln Val Cys Arg Val Val Pro Leu Val Ala Gly Gly Ile Cys Gln Cys
            35                  40                  45

Leu Ala Glu Arg Tyr Ser Val Ile Leu Leu Asp Thr Leu Leu Gly Arg
        50                  55                  60

Met Leu Pro Gln Leu Val Cys Arg Leu Val Leu Arg Cys Ser
65                  70                  75

<210> SEQ ID NO 7
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Tyr Trp Leu Tyr Arg Ala Leu Ile Lys Arg Ile Gln Ala Leu Ile
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Trp Leu Tyr Arg Ala Leu Ile Lys Arg Ile Gln Ala Leu Ile
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Trp Leu Tyr Arg Ala Leu Ile Lys Arg Ile Gln Ala Leu Ile
1               5                   10                  15

<210> SEQ ID NO 10
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Phe Trp Leu Tyr Arg Ala Leu Ile Lys Arg Ile Gln Ala Leu Ile
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11
```

Arg Leu Leu Pro Gln Leu Val Tyr Arg Leu Val Leu Arg Tyr Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Met Leu Pro Gln Leu Val Tyr Arg Leu Val Leu Arg Leu Ser
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Met Leu Pro Gln Leu Val Tyr Arg Leu Val Leu Arg Ala Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Met Leu Pro Gln Leu Val Tyr Arg Leu Val Leu Arg Phe Ser
1               5                   10                  15

<210> SEQ ID NO 15
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Phe Pro Ile Pro Leu Pro Tyr Tyr Trp Leu Tyr Arg Ala Leu Ile Lys
1               5                   10                  15

Arg Ile Gln Ala Leu Ile Pro Lys Gly Gly Arg Leu Leu Pro Gln Leu
            20                  25                  30

Val Tyr Arg Leu Val Leu Arg Tyr Ser
        35                  40

<210> SEQ ID NO 16
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Phe Pro Ile Pro Leu Pro Tyr Leu Trp Leu Tyr Arg Ala Leu Ile Lys
1               5                   10                  15

```
Arg Ile Gln Ala Leu Ile Pro Lys Gly Gly Arg Met Leu Pro Gln Leu
            20                  25                  30

Val Tyr Arg Leu Val Leu Arg Leu Ser
            35                  40

<210> SEQ ID NO 17
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Phe Pro Ile Pro Leu Pro Tyr Ala Trp Leu Tyr Arg Ala Leu Ile Lys
1               5                   10                  15

Arg Ile Gln Ala Leu Ile Pro Lys Gly Gly Arg Met Leu Pro Gln Leu
            20                  25                  30

Val Tyr Arg Leu Val Leu Arg Ala Ser
            35                  40

<210> SEQ ID NO 18
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Phe Pro Ile Pro Leu Pro Tyr Phe Trp Leu Tyr Arg Ala Leu Ile Lys
1               5                   10                  15

Arg Ile Gln Ala Leu Ile Pro Lys Gly Gly Arg Met Leu Pro Gln Leu
            20                  25                  30

Val Tyr Arg Leu Val Leu Arg Phe Ser
            35                  40

<210> SEQ ID NO 19
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Phe Pro Ile Pro Leu Pro Tyr Tyr Trp Leu Tyr Arg Ala Leu Ile Lys
1               5                   10                  15

Arg Ile Gln Ala Leu Ile Asp Ala Thr Lys Arg Leu Leu Pro Gln Leu
            20                  25                  30

Val Tyr Arg Leu Val Leu Arg Tyr Ser
            35                  40

<210> SEQ ID NO 20
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Phe Pro Ile Pro Leu Pro Tyr Leu Trp Leu Tyr Arg Ala Leu Ile Lys
1               5                   10                  15
```

Arg Ile Gln Ala Leu Ile Asp Ala Thr Lys Arg Met Leu Pro Gln Leu
            20                  25                  30

Val Tyr Arg Leu Val Leu Arg Leu Ser
        35                  40

<210> SEQ ID NO 21
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Phe Pro Ile Pro Leu Pro Tyr Ala Trp Leu Tyr Arg Ala Leu Ile Lys
1               5                   10                  15

Arg Ile Gln Ala Leu Ile Asp Ala Thr Lys Arg Met Leu Pro Gln Leu
            20                  25                  30

Val Tyr Arg Leu Val Leu Arg Ala Ser
        35                  40

<210> SEQ ID NO 22
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Phe Pro Ile Pro Leu Pro Tyr Phe Trp Leu Tyr Arg Ala Leu Ile Lys
1               5                   10                  15

Arg Ile Gln Ala Leu Ile Asp Ala Thr Lys Arg Met Leu Pro Gln Leu
            20                  25                  30

Val Tyr Arg Leu Val Leu Arg Phe Ser
        35                  40

<210> SEQ ID NO 23
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Phe Pro Ile Pro Leu Pro Tyr Cys Trp Leu Tyr Arg Ala Leu Ile Lys
1               5                   10                  15

Arg Ile Gln Ala Met Ile Pro Lys Gly Gly Arg Met Leu Pro Gln Leu
            20                  25                  30

Val Tyr Arg Leu Val Leu Arg Cys Ser
        35                  40

<210> SEQ ID NO 24
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Phe Pro Ile Pro Leu Pro Tyr Cys Trp Leu Tyr Arg Ala Leu Ile Lys

```
1               5                   10                  15
Arg Ile Gln Ala Met Ile Asp Ala Thr Lys Arg Met Leu Pro Gln Leu
            20                  25                  30

Val Tyr Arg Leu Val Leu Arg Cys Ser
            35                  40

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Any amino acid but at least one amino acid at
      position 1 or 4 is not cysteine
<220> FEATURE:
<221> NAME/KEY: MOD_RES
<222> LOCATION: (4)..(4)
<223> OTHER INFORMATION: Any amino acid but at least one amino acid at
      position 1 or 4 is not cysteine
<220> FEATURE:
<221> NAME/KEY: MOD_RES
<222> LOCATION: (14)..(14)
<223> OTHER INFORMATION: Any amino acid
<220> FEATURE:
<223> OTHER INFORMATION: See specification as filed for detailed
      description of substitutions and preferred embodiments

<400> SEQUENCE: 25

Xaa Trp Leu Xaa Arg Ala Leu Ile Lys Arg Ile Gln Ala Xaa Ile
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Any amino acid
<220> FEATURE:
<221> NAME/KEY: MOD_RES
<222> LOCATION: (8)..(8)
<223> OTHER INFORMATION: Any amino acid but at least one amino acid at
      position 8 or 14 is not cysteine
<220> FEATURE:
<221> NAME/KEY: MOD_RES
<222> LOCATION: (14)..(14)
<223> OTHER INFORMATION: Any amino acid but at least one amino acid at
      position 8 or 14 is not cysteine
<220> FEATURE:
<223> OTHER INFORMATION: See specification as filed for detailed
      description of substitutions and preferred embodiments

<400> SEQUENCE: 26

Arg Xaa Leu Pro Gln Leu Val Xaa Arg Leu Val Leu Arg Xaa Ser
1               5                   10                  15
```

COMPOSITIONS AND METHOD FOR ADMINISTERING PPARGAMMA AGONISTS, SURFACTANT PEPTIDES AND PHOSOPHOLIPIDS

CROSS REFERENCE TO RELATED APPLICATIONS

This application is a national stage of International Application No. PCT/US2017/020881 filed Mar. 6, 2017, which claims the benefit of U.S. Provisional Application No. 62/304,845, filed Mar. 7, 2016, the content of which is incorporated by reference in its entirety into the present disclosure.

SEQUENCE LISTING

The instant application contains a sequence listing which has been submitted in ascii format via EFS-web and is hereby incorporated by reference in its entirety. Said ascii copy, created on Sep. 4, 2018, is named 0WVR-224652-US_SL.TXT and is 11,515 bytes in size.

FIELD

The present disclosure relates to compositions and therapies that can address both the symptoms and disorders associated with insufficient surfactant production and hyperoxia. The composition can comprise one or more of the following: a PPAR gamma agonist, a surfactant peptide, and one or more phospholipids.

BACKGROUND

For newborns to be able to breathe easily, the air sacs (alveoli) in the lungs must be able to remain open and to be filled with oxygen. This requires the presence of endogenous surfactant that coats the surface of the air sacs to allow them to remain open during the respiratory cycle. Physiologically adequate Endogenous surfactant production, however, typically begins after about 32 weeks of gestation. Thus, premature infants that are born around or before 32 weeks of gestation are more likely to lack the ability to produce sufficient lung surfactant and therefore develop respiratory distress syndrome (RDS). RDS is a breathing disorder in which the air sacs do not remain open due to the lack or insufficient production of endogenous surfactant.

Premature infants are often administered exogenous surfactant concomitant to oxygen therapy. While administration of exogenous surfactant has been demonstrated to be effective in treating RDS, it has not been demonstrated to be effective in reducing the incidence of certain other lung diseases, particularly those which are associated with hyperoxia such as delayed or diminished lung maturation and bronchopulmonary dysplasia (BPD). BPD is a form of chronic lung disease that results from damage to the lungs caused by mechanical ventilation (respirator), long-term use of oxygen, infection, etc. Most infants recover from BPD, but some may have long-term breathing difficulty.

What is therefore needed is a therapy that can be used to treat the adverse symptoms or disorders of the lungs associated with both insufficient surfactant production and exposure to conditions such as hyperoxia and infection.

SUMMARY

The present disclosure provides compositions and therapies that can address both the symptoms and disorders associated with insufficient surfactant production and hyperoxia. In one embodiment, the composition can be formulated for aerosol delivery during ventilation therapy. The composition can comprise one or more of the following: a PPAR gamma agonist, a surfactant peptide, and one or more phospholipids. The compositions are formulated to provide the complementary benefits of reducing the likelihood of developing RDS, or the severity of RDS in infants, as well as protecting and promoting lung maturation in a hyperoxic environment. Aerosol delivery of this formulation is believed to effectively block neonatally-induced lung injury and prevent BPD in patients exposed to hyperoxia and therefore provide a therapeutic effect that is greater than would be expected with either the PPAR gamma agonist alone, or the combination of the surfactant peptide and phospholipids.

Administration of surfactant compositions comprising the surfactant peptide and one or more phospholipids, while effective in treating RDS, has not been demonstrated to be effective in protecting against disruptions to lung development, maturation and injury repair. Administration of PPAR gamma agonists, however, is believed to promote lung development, maturation and injury repair and also to prevent or protect against hyperoxia-induced lung injury. This is because lung mesenchymal PPAR gamma expression is believed to have a central role in driving alveolar epithelial-mesenchymal interactions that are fundamental to lung maturation.

The compositions generally comprise one or a combination of a PPAR gamma agonist, one or more surfactant peptides and one or more phospholipids. It is understood that the surfactant peptides are not limited to the specific synthetic surfactant peptides described herein, but may also include other synthetic surfactant peptides, natural surfactant peptides, and any combination thereof.

In one embodiment, the PPAR gamma agonist may be a thiozolidinedione (TZD). The TZD can be selected from the group consisting of: a rosiglitazone, a troglitazone, a farglitazar, a phenylacetic acid, a GW590735, a GW677954, a GW1929, an S2648, an Avandia, an Avandamet, a ciglitazone, a pioglitazone, an adaglitazone, a 15 deoxy prostaglandin J2, a 15-deoxy-delta12,14 PGJ2, GW-9662, a MCC-555, a LG100754, an nTZDpa, and a Telmisartan.

In one optional aspect, the PPAR gamma agonist can selectively modulate PPAR gamma. The PPAR gamma agonist can be one or both of L312 and KDR-629800.

In another optional aspect, the PPAR gamma agonist can be an endogenous natural compounds with PPAR gamma activity or a metabolite thereof. The PPAR gamma agonist can be selected from the group consisting of: 15-deoxy prostaglandin J2, 15-deoxy-deltal-2, 14 PGJ2, 9-HODE, 12-HETE, 15-HETE, and 1-O-hexadecyl-2-Azelaoyl-sn-glycero-3-phosphocholine.

In another optional aspect, the PPAR gamma agonist can be one or both of a dual and pan PPAR gamma agonists. The PPAR gamma agonist can be a glitazar. The glitazar can be one or more selected from the group consisting of: aleglitazar, muraglitazar, tesaglitazar, and saroglitazar.

In another optional aspect, the PPAR gamma agonist can be a triterpenoid. The triterpenoid can be one or more selected from the group consisting of: ursolic and oleanolic acid, betulinic acid, celastrol, pristimerin, lupeol, avicins, synthetic triterpenoid derivatives, 2-cyano-3,12-dioxooleana-1,9 (11)-dien-28-oic (CDDO), its methyl ester (CDDO-Me), and imidazolide (CDDO-Im) derivatives.

In another optional aspect, the PPAR gamma agonist can be a PPAR gamma dietary nutraceutical selected from the group consisting of: curcumin, n-3 and n-6 fatty acids and their derivatives, isoflavones, and flavonoids.

In another embodiment, the surfactant peptides are those that can be used in combination with phospholipids and the PPAR gamma agonists. Exemplary surfactant peptides that can be used in the compositions with the PPAR gamma agonist and the phospholipids can include peptides that comprise an N-terminal helix, connected optionally through a turn, to a C-terminal helix of the alpha helix of surfactant protein (SP)-B. The N-terminal or C-terminal helices can be modified, as compared to the natural SP-B peptide, with one or more substitutions at the cysteine and/or methionine residues. In some embodiments, the turn can be a natural or designer loop peptide sequence that facilitates formation of a helix-turn-helix structure.

Table A below lists the amino acid sequences, SEQ ID NOs and, in some cases, short names for various peptides disclosed in the present application.

The B-YCL peptide (SEQ ID NO: 23) and B-DATK-YCL peptide (SEQ ID NO: 24) have amino acid sequences in which the cys8 and cys40 are blocked or have an acetamidomethyl modification in which the thiol group on the cysteine is methylated via an acetamidomethyl group to selectively form disulfide bridges.

In one optional aspect, at least one of the one or more surfactant peptides comprises: (i) a first fragment comprising the amino acid sequence of XWLXRALIKRIQAZI (SEQ ID NO: 1) or a first amino acid sequence having at least 90% sequence identity to SEQ ID NO: 1 and (ii) a second fragment comprising the amino acid sequence of RZLPQLVXRLVLRXS (SEQ ID NO: 2) or a second amino acid sequence having at least 90% sequence identity to SEQ ID NO: 2, wherein (a) X is any amino acid but at least one amino acid at the X positions is not cysteine, or (b) Z is any amino acid but at least one amino acid at the Z positions is

TABLE A

Peptide Sequences and Names

| | |
|---|---|
| SEQ ID NO: 1 | XWLYRALIKRIQAZI |
| SEQ ID NO: 2 | RZLPQLVYRLVLRXS |
| SEQ ID NO: 3 | PKGG |
| SEQ ID NO: 4 | DATK |
| SEQ ID NO: 5 | FPIPLPY |
| SEQ ID NO: 7 | YWLYRALIKRIQALI |
| SEQ ID NO: 8 | LWLYRALIKRIQALI |
| SEQ ID NO: 9 | AWLYRALIKRIQALI |
| SEQ ID NO: 10 | FWLYRALIKRIQALI |
| SEQ ID NO: 11 | RLLPQLVYRLVLRYS |
| SEQ ID NO: 12 | RMLPQLVYRLVLRLS |
| SEQ ID NO: 13 | RMLPQLVYRLVLRAS |
| SEQ ID NO: 14 | RMLPQLVYRLVLRFS |

Alpha-helix of SP-B:
FPIPLPYCWLCRALIKRIQAMIPKGALAVAVAQVCRVVPLVAGGICQCLAERYSVILLDTLLGRMLPQ
LVCRLVLRCS (SEQ ID NO: 6)

| | | | |
|---|---|---|---|
| B-YL: | FPIPLPY | YWLYRALIKRIQALIPKGG | RLLPQLVYRLVLRYS(SEQ ID NO: 15) |
| B-YLL: | FPIPLPY | LWLYRALIKRIQALIPKGG | RMLPQLVYRLVLRLS(SEQ ID NO: 16) |
| B-YAL: | FPIPLPY | AWLYRALIKRIQALIPKGG | RMLPQLVYRLVLRAS(SEQ ID NO: 17) |
| B-YFL: | FPIPLPY | FWLYRALIKRIQALIPKGG | RMLPQLVYRLVLRFS(SEQ ID NO: 18) |
| B-DATK-YL: | FPIPLPY | YWLYRALIKRIQALIDATK | RLLPQLVYRLVLRYS(SEQ ID NO: 19) |
| B-DATK-YLL: | FPIPLPY | LWLYRALIKRIQALIDATK | RMLPQLVYRLVLRLS(SEQ ID NO: 20) |
| B-DATK-YAL: | FPIPLPY | AWLYRALIKRIQALIDATK | RMLPQLVYRLVLRAS(SEQ ID NO: 21) |
| B-DATK-YFL: | FPIPLPY | FWLYRALIKRIQALIDATK | RMLPQLVYRLVLRFS(SEQ ID NO: 22) |
| B-YCL: | FPIPLPY | CWLYRALIKRIQAMIPKGG | RMLPQLVYRLVLRCS(SEQ ID NO: 23) |
| B-DATK-YCL | FPIPLPY | CWLYRALIKRIQAMIDATK | RMLPQLVYRLVLRCS(SEQ ID NO: 24) | not methionine. The surfactant peptide can further comprise (iii) a turn between the first fragment and the second fragment.

In one optional aspect, the turn can comprise PKGG (SEQ ID NO: 3).

In another optional aspect, the turn can form a salt bridge between amino acids within the turn or between the turn and the first or second fragment.

In another optional aspect, the turn can comprise DATK (SEQ ID NO: 4).

In another optional aspect, the first fragment is at the N-terminal end of the second fragment.

In another optional aspect, the surfactant peptide can further comprise an insertion sequence at the N-terminal end of the first fragment. The insertion sequence can comprise FPIPLPY (SEQ ID NO: 5).

In another optional aspect, the surfactant peptide can be 100, 95, 90, 85, 80, 75, 70, 65, 60, 55, 50, 45, 40, 35, 30, 25, 20, 15, or 10 amino acids in length or shorter. The surfactant peptide can also have an amino acid length between any two of the foregoing values.

In another optional aspect, the at least one amino acid at the X positions of the surfactant peptide is not cysteine.

In another optional aspect, each amino acid at the X positions of the surfactant peptide is not cysteine.

In another optional aspect, the amino acid at each X position of the surfactant peptide can be selected from the group consisting of Y, L, A, and F.

In another optional aspect, at least one amino acid at the Z positions of the surfactant peptide is not methionine.

In another optional aspect, each amino acid at the Z position of the surfactant peptide is not methionine.

In another optional aspect, the amino acid at each X position of the surfactant peptide is leucine.

In a further embodiment, the one or more phospholipids can be included in the composition. The one or more phosopholipids can be selected from the group consisting of dipalmitoylphosphatidylcholine (DPPC), palmitoyloleoylphosphatidylcholine (POPC), phosphatidylglycerol (PG), palmitoyloleoylphosphatidylglycerol (POPG), cholesterol (Chol), 1,2-Dioleoyl-sn-glycero-3-phosphocholine (DOPC), 1-Palmitoyl-2-oleoyl-sn-glycero-3-phosphoethanolamine (POPE), 1-palmitoyl-2-oleoylsn-glycero phosphocholine (POPS), 1,2-Distearoyl-sn-glycero-3-phosphocholine (DSPC), 1,2-Dipalmitoyl-sn-glycero-3-phosphoethanolamine (DPPE), 1,2-dipalmitoyl-sn-glycero-3-phosphoglycerol (DPPG), DEPN-8, PG-1, and combinations thereof.

In one optional aspect, the one or more phospholipid can comprise DPPC, POPC, and POPG.

In another optional aspect, the DPPC, POPC, and POPG are at ratio of about (4-6):(2-4):(1-3).

Also provided, in one embodiment, is a method of treatment comprising administration to a patient in need thereof a composition of the present disclosure. In some aspects, the surfactant deficiency or dysfunction comprises a respiratory distress syndrome in an infant or a respiratory distress syndrome secondary to surfactant deficiency or lung immaturity in a premature or near-term infant. Also provided is a method of treating surfactant deficiency or dysfunction in a patient in need thereof, comprising administration to the patient a PPAR gamma agonist; one or more surfactant peptides; and one or more phospholipids. The PPAR gamma agonist, the one or more surfactant peptides and the one or more phospholipids may be administered concurrently or sequentially.

BRIEF DESCRIPTION OF THE DRAWINGS

FIGS. 1A-1D are bar graphs showing that fetal rat lung explants treated with a composition comprising a PPAR gamma agonist, pioglitazone (PGZ), the synthetic surfactant B-YL and phospholipids demonstrated increases in the expression of markers for lung maturation at the three different concentrations of PGZ. FIGS. 1A-1C demonstrate the increased expression of PPARγ (FIG. 1A), surfactant protein SP-C (FIG. 1B), and cholinephosphate cytidylyltransferase (CCT)-α protein levels (FIG. 1C), as demonstrated by Western blot analysis. Additionally, FIG. 1D demonstrates a significant increase in [3H]choline incorporation into disaturated phosphatidylcholine, $p<0.05$ vs. control, n=3.

FIGS. 3A-3C are bar graphs showing that concomitant administration of nebulized PGZ, B-YL and phospholipids resulted in hyperoxia-induced alterations in the apoptosis marker BcL2/Bax ratio (FIG. 3A) and blocking of inflammatory markers IL-6 (FIG. 3B) and IF-γ (FIG. 3C).

FIGS. 4A-4C are representative immunostaining pictures in which the red stained areas showed hyperoxia-induced activation in TGF-β (as determined by ALKS protein levels) and in which the green stained areas showed the blocking of Wnt signaling, by concomitant administration of PGZ, B-YL, and phospholipids.

DETAILED DESCRIPTION

Figures 2A, 2B, 2C:
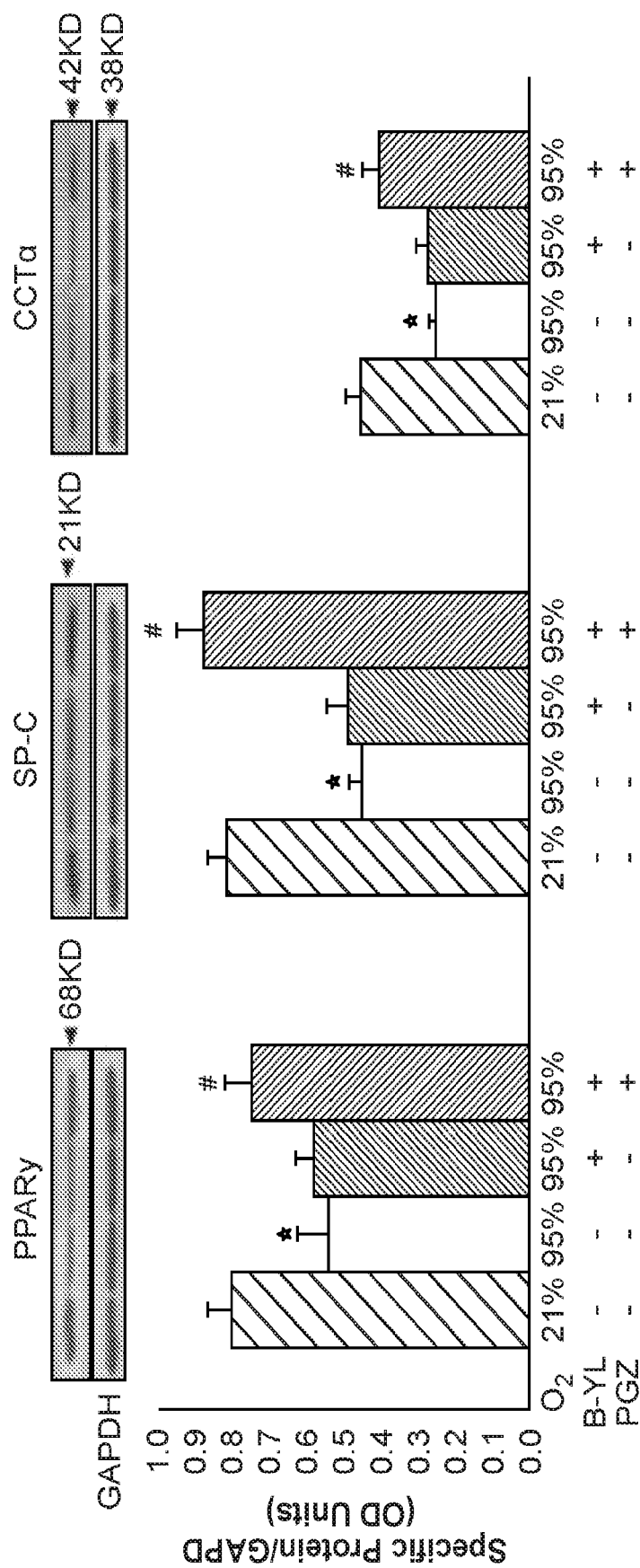
FIGS. 2A-2F are bar graphs showing that concomitant administration of nebulized PGZ, B-YL and phospholipids resulted in decreases in the expression of markers for lung injury such as epithelial and mesenchymal markers of alveolar differentiation, such as hyperoxia-induced decreases in PPARγ (FIG. 2A), SP-C surfactant protein (FIG. 2B), CCT-α (FIG. 2C). Moreover, increases in the expression of LEF-1 (FIG. 2D), fibronectin (FIG. 2E) were blocked by concomitant administration of PGZ, B-YL, and phospholipids. Hyperoxia-induced decrease in triolein uptake was also blocked by concomitant administration of PGZ, B-YL, and phospholipids (FIG. 2F).

It is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a peptide" includes a plurality of peptides.

1. Definitions

Unless defined otherwise, all technical and scientific terms used herein have the same meaning as commonly understood by one of ordinary skill in the art to which this disclosure belongs. As used herein the following terms have the following meanings.

The term "about" when used before a numerical designation, e.g., temperature, time, amount, and concentration, including range, indicates approximations which may vary by (+) or (−) 10%, 5% or 1%.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

As used herein, the term "hyperoxic" can refer to conditions that produce elevated $pO_2$ in a mammal as compared to the same mammal exposed to normal atmosphere (e.g. about 20% O2). In certain embodiments, hyperoxic conditions comprise about 21% or more, 30% or more, 50% or more, 75% or more, 90% or more, 95% or more O2, and within a range of any two of the foregoing percentages.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure.

Likewise, the present disclosure also includes sequences that have one, two, three, four, or five substitutions, deletions or addition of amino acid residues or nucleotides as compared to the reference sequences.

In any of the embodiments described herein, analogs of a peptide comprising any amino acid sequence described herein are also provided, which have at least about 80%, or at least about 83%, or at least about 85%, or at least about 90%, or at least about 95%, or at least about 98%, or at least about 99% sequence identity to any of reference amino acid sequences. In some embodiments, the analogs include one, two, three, four, or five substitution, deletion or addition of amino acid residues as compared to the reference sequences. In some embodiments, the substitution is a conservative substitution.

As is well-known in the art, a "conservative substitution" of an amino acid or a "conservative substitution variant" of a peptide include, but are not limited to, an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table B.

TABLE B

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | (a) Val, D-Val, Met, D-Met, D-Ile, D-Leu, Ile |
| Lysine | D-Lys, Arg, D-Arg, Orn, D-Orn |
| Methionine | (b) D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | (c) D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution.

As used herein, the term "pharmaceutically acceptable" includes, but is not limited to, that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" includes, but is not limited to, pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the internal surface of the lung.

As used herein, the terms "patient in need thereof" includes, but is not limited to, pre-term infants (less than 37, 36 weeks or less, 35 weeks or less, 34 weeks or less, 33 weeks or less, 32 weeks or less, 31 weeks or less, 30 weeks or less, 29 weeks or less, 28 weeks or less, 27 weeks or less, 26 weeks or less, 25 weeks or less, 24 weeks or less, 23 weeks or less, 22 weeks or less, 21 weeks or less, 20 weeks or less, 19 weeks or less, 18 weeks or less, 17 weeks or less, 16 weeks or less of gestation or between any two of the foregoing values), full-term infants (37-42 weeks gestation), infants between the ages of 0 months to 12 months, children between the ages of 1 to 18 years of age, adults over 18 years of age, including young adults between the ages of 18 to 35, middle-aged adults between the ages of 36-69 and elderly adults 70 years of age and older. The "patient in need thereof" may have any one or more of the following conditions: lung immaturity, lung surfactant deficiency, fluid-filled lungs, lung injury resulting from ventilation treatment, including mechanical or continuous positive airway pressure (CPAP) ventilators, hyperoxia-induced lung injury, acute lung injury, respiratory distress syndrome (RDS), chronic lung injury, chronic bronchopulmonary dysplasia (BPD), downregulation of pulmonary mesenchymal PPAR gamma, upregulation of myogenic signaling pathways, transdifferentiation of lipid-rich alveolar interstitial fibroblasts to myofibroblasts, asthma, nicotine exposure-induced lung injuries, nicotine exposure-induced asthma, insufficient alveolar development of the lungs, and insufficient vascular development of the lungs.

2. PPARγ Agonists

PPAR gamma agonists are believed to significantly enhance lung maturation when administered to a patient in need thereof.

PPAR gamma agonists can include PPAR gamma specific ligands and/or ligands that activate receptors other than PPAR gamma (e.g. PPAR beta). PPAR gamma ligands can include thiozolidinediones (TZD), selective PPAR gamma modulating drugs, endogenous natural compounds with PPAR gamma activity and their metabolites, dual and pan PPAR gamma agonists, triterpenoids, NSAID and indoles, and PPAR gamma dietary nutraceuticals.

TZD compounds include but are not limited to, rosiglitazone, troglitazone (Resulin), farglitazar, phenylacetic acid, GW590735, GW677954, GW1929, 52648, Avandia, Avandamet (avandia+metformin), ciglitazone, pioglitazone (Actos), adaglitazone, 15 deoxy prostaglandin J2 (15PGJ2), 15-deoxy-delta12,14 PGJ2, GW-9662, MCC-555 (RWJ241947, Netoglitazone, Isaglitazone), LG100754, nTZDpa, and Telmisartan, to name a few.

Selective PPAR gamma modulating drugs include, but are not limited to, L312 and KDR-629800.

Endogenous natural compounds with PPAR gamma activity and their metabolites include, but are not limited to, 15 deoxy prostaglandin J2 (15PGJJ2), 15-deoxy-deltal-2, 14 PGJ2, 9-HODE, 12-HETE, 15-HETE, 1-O-hexadecyl-2-Azelaoyl-sn-glycero-3-phosphocholine (AZ-PC), to name a few.

Dual and pan PPAR gamma agonist include, but are not limited to, glitazars such as, for example, aleglitazar, muraglitazar, tesaglitazar, saroglitazar, to name a few.

Triterpenoids are characterized by a basic backbone modified in various ways include, but are not limited to, ursolic and oleanolic acid, betulinic acid, celastrol, pristimerin, lupeol, avicins, synthetic triterpenoid derivatives, including 2-cyano-3,12-dioxooleana-1,9 (11)-dien-28-oic (CDDO), its methyl ester (CDDO-Me), and imidazolide (CDDO-Im) derivatives.

PPAR gamma dietary nutraceuticals, including curcumin, n-3 and n-6 fatty acids and their derivatives, isoflavones, and flavonoids.

3. Surfactant Peptides

In one embodiment, the present disclosure provides surfactant peptides. In one embodiment, the peptide includes an N-terminal helix, connected optionally through a turn, to a C-terminal helix of the alpha helix of surfactant protein (SP)-B. The N-terminal or C-terminal helix can be modified, as compared to the natural SP-B peptide, with one or more substitutions at the cysteine and/or methionine residues. In some embodiments, the turn is a natural or designer loop peptide sequence that facilitates formation of a helix-turn-helix structure.

The sequence of the alpha-helix of SP-B is provided in Table A (SEQ ID NO: 6), where the N-terminal helix and the C-terminal helix are underlined.

The peptides (SEQ ID NO: 11-14) can be modified by replacing the PKGG turn with another turn, such as DATK (SEQ ID NO: 4) which is discovered to be able to increase molecular stability and improve the ease of synthesis, folding and purification of the peptides (SEQ ID NO: 15-18).

In some embodiments, any of these amino acid sequences can further be modified within either or both the helix regions. In one embodiment, at least one, two, three, or four, or all of the cysteines in the helix is substituted with another amino acid. In one embodiment, at least one cysteine in each helix is substituted with another amino acid. In one embodiment, at least one of the helices has no cysteine residue. In one embodiment, the entire peptide includes no cysteine. In some embodiments, the substitution is with Y, L, A, or F.

Surprisingly, it is discovered that, even when the cysteines are substituted resulting in removal of the disulfide bonds, the peptide can still form a desired helix-turn-helix structure and is more stable and effective. In some examples, when the cysteines are substituted with one or more tyrosine residues, the hydrophobic core formed by the tyrosine residues can further help stabilize the peptide.

In one embodiment, at least one of the methionine residues is substituted with another amino acid. In one embodiment, both of the methionine residues are substituted. In some embodiments, the substitution is with leucine. Also surprisingly, such a substitution does not change the structure of the peptide but rather makes it more stable and easier to fold and manufacture. Further, the removal of methionine renders the peptide resisting oxidative stress.

In one embodiment, provided is an isolated peptide comprising (i) a first fragment comprising the amino acid sequence of XWLYRALIKRIQAZI (SEQ ID NO: 1) or a first amino acid sequence having at least 90% (or at least 80%, 85% or 95%) sequence identity to SEQ ID NO: 1 and (ii) a second fragment comprising the amino acid sequence of RZLPQLVYRLVLRXS (SEQ ID NO: 2) or a second amino acid sequence having at least 90% (or at least 80%, 85% or 95%) sequence identity to SEQ ID NO: 2, wherein: (a) X is any amino acid but at least one amino acid at the X positions is not cysteine, or (b) Z is any amino acid but at least one amino acid at the Z positions is not methionine.

Non-limiting examples of SEQ ID NO: 1 include SEQ ID NOS: 7-10. Non-limiting examples of SEQ ID NO: 2 include SEQ ID NO: 11-14.

In some embodiments, the peptide further includes a turn between the first fragment and the second fragment. A "turn" as used herein, refers to a relatively short (e.g., less than 50 amino acids in length) amino acid fragment that forms a secondary structure in a polypeptide chain where the polypeptide chain reverses its overall direction. Examples of turns include, without limitation, α-turns, β-turns, γ-turns, δ-turns, π-turns, loops, multiple turns and hairpins. The turn is typically from one amino acid to about 50 amino acids (or to about 45, 40, 35, 30, 25, 20, 15, 10, 9, 8, 7, 6 or 5 amino acids) in length. In some embodiments, the turn does not include cysteine. In some embodiments, the turn does not include methionine.

In some embodiments, the turn includes an amino acid that forms a salt bridge with either of the helices. In some embodiments, the turn includes amino acids to form a salt bridge within.

Non-limiting examples of turns include PKGG (SEQ ID NO: 3), DATK (SEQ ID NO: 4) and amino acids 23-63 of SEQ ID NO: 6 or a portion or combination of portions thereof.

It is contemplated that the helices can be orientated either way. In one embodiment, SEQ ID NO: 1 (or the first fragment) can be at the N-terminal direction of SEQ ID NO: 2 (or the second fragment). In one embodiment, SEQ ID NO: 1 (or the first fragment) can be at the C-terminal direction of SEQ ID NO: 2 (or the second fragment).

In some embodiments, the peptide further includes an insertion sequence at the N-terminal end of the peptide. In some embodiments, the peptide further includes an insertion sequence at the N-terminal direction of the first fragment or the N-terminal direction of the second fragment. The insertion sequence, in some embodiments, includes at least one proline. In another embodiment, the insertion sequence includes at least a leucine or isoleucine. A non-limiting example of the insertion sequence is FPIPLPY (SEQ ID NO: 5).

The total length of the peptide varies from 20 amino acids to about 100 amino acids. In one embodiment, the peptide is not longer than about 100, or 90, 80, 70, 60 or 50 amino acids long.

Non-limiting examples of the peptides include SEQ ID NO: 15-24 or an amino acid sequence having at least 90% (or at least 80%, 85% or 95%) sequence identity to any amino acid sequence of SEQ ID NO: 15-24, or an amino acid sequence derived from any amino acid sequence of SEQ ID NO: 15-24 with one, two or three amino acid addition, deletion and/or substitution.

4. Synthesis of Surfactant Peptides

The peptides described herein can be ordered from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification. Recombinant DNA technology methods are described in Sambrook et al., "Molecular Cloning: A Laboratory Manual", 3rd Edition, Cold Spring Harbor Laboratory Press, (2001), incorporated herein by reference, and are well known to the skilled biochemist.

The peptides can be also prepared by using recombinant expression systems. Generally, this involves inserting the nucleic acid molecule into an expression system to which the molecule is heterologous (i.e., not normally present). One or more desired nucleic acid molecules encoding a peptide of the disclosure may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

The nucleic acid molecules can be derived from the known SP-B nucleotides. In certain embodiments, it may be desirable to prepare codon-enhanced nucleic acids that will favor expression of the desired peptide in the transgenic expression system of choice.

The preparation of the nucleic acid constructs can be carried out using methods well known in the art. U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture. Other vectors are also suitable.

Once a suitable expression vector is selected, the desired nucleic acid sequences are cloned into the vector using standard cloning procedures in the art. The vector is then introduced to a suitable host.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by high-performance liquid chromatography (HPLC).

Alternatively, if the peptide of interest is not secreted, it can be isolated from the recombinant cells using standard isolation and purification schemes. This includes disrupting the cells (e.g., by sonication, freezing, French press, etc.) and then recovering the peptide from the cellular debris. Purification can be achieved using the centrifugation, precipitation, and purification procedures described above.

Whether the peptide of interest is secreted or not, it may also contain a purification tag (such as poly-histidine, a glutathione-5-transferase, or maltose-binding protein (MBP)), which assists in the purification but can later be removed, i.e., cleaved from the peptide following recovery. Protease-specific cleavage sites can be introduced between the purification tag and the desired peptide. The desired peptide product can be purified further to remove the cleaved purification tags.

5. Phospholipids

One or more lipids may be included in the compositions described herein. The one or more lipids can include phospholipids and the phospholipids can include synthetic ester-linked phospholipids, phospholipase-resistant phospholipids, phospholipids, naturally occurring phospholipids, or a mixture of any of the foregoing. There are an abundance of kinds of lipids and phospholipids suitable for use in surfactants.

Non-limiting examples of phospholipids include dipalmitoylphosphatidylcholine (DPPC), palmitoyloleoylphosphatidylcholine (POPC), phosphatidylglycerol (PG), palmitoyloleoylphosphatidylglycerol (POPG), cholesterol (Chol), glycerophospholipids such as 1,2-Dioleoyl-sn-glycero-3-phosphocholine (DOPC), 1-Palmitoyl-2-oleoyl-sn-glycero-3-phosphoethanolamine (POPE), 1-palmitoyl-2-oleoylsn-glycero phosphocholine (POPS), 1,2-Distearoyl-sn-glycero-3-phosphocholine (DSPC), 1,2-Dipalmitoyl-sn-glycero-3-phosphoethanolamine (DPPE), 1,2-dipalmitoyl-sn-glycero-3-phosphoglycerol (DPPG) and diether phosphonolipid analogs of DPPC and phosphatidylglycerol (e.g., DEPN-8 and PG-1). The phospholipids may be provided in any one or a combination of the foregoing various amount ratios.

The one or more phospholipids can also be provided in form of a racemic mixture, containing substantially equivalent amounts of stereoisomers. In another embodiment, the phospholipids can be prepared or otherwise isolated, using known procedures, to obtain a single stereoisomer substantially free of its corresponding stereoisomer (i.e., substantially pure). By substantially pure, it is intended that a stereoisomer is at least about 95% pure, more preferably at least about 98% pure, most preferably at least about 99% pure. Both racemic mixtures and substantially pure stereoisomers of the phospholipase-resistant lipid compounds can be used in the compositions described herein.

6. Compositions and Formulations of PPARγ and Surfactants

The present disclosure provides compositions that can include any one or a combination of one or more PPAR gamma agonists, one or more surfactant peptides, and one or more phospholipids as described herein. In some embodiments, the composition includes at least two different phospholipids, at least three different phospholipids, at least four different phospholipids, or at least five different phospholipids. In some embodiments, the composition includes no more than eight different phospholipids, no more than seven different phospholipids, no more than six different phospholipids, or no more than five different phospholipids.

The phospholipids can be mixed at suitable ratios, in some embodiments. For instance, DPPC:POPC:POPG can be used a ratio of about 5:3:2, DPPC:POPG at a ratio of about 7:3, DEPN-8:PG-1 at about 9:1 or 8:2. In a particular example, the phospholipids include DPPC, POPC, and POPG. In another example, the phospholipids include DPPC and POPC. In another example, the phospholipids include DPPC and POPG. In another example, the phospholipids include POPC and POPG. In another example, the phospholipids include DPPC, POPC, POPG, DEPN-8, and PG-1. In another example, the phospholipids include DPPC, POPC, POPG, and DEPN-8. In another example, the phospholipids include DPPC, POPC, POPG, and PG-1. In another example, the phospholipids include DPPC, POPC, and DEPN-8. In another example, the phospholipids include DPPC, POPG, and DEPN-8. In another example, the phospholipids include POPC, POPG, and DEPN-8. In another example, the phospholipids include DPPC, POPC, and PG-1. In another example, the phospholipids include DPPC, POPG, and PG-1. In another example, the phospholipids include POPC, POPG, and PG-1. In one aspect, the DPPC, POPC, and POPG are at ratio of about (4-6):(2-4):(1-3). In another aspect, the DPPC, POPC, and POPG are at ratio of about (2-8):(1-6):(1-6). In another aspect, the DPPC, POPC, and POPG are at ratio of about (1-10):(1-8):(1-8). In another aspect, the DPPC, POPC, and POPG are at ratio of about (4-5):(2-4):(1-3). In another aspect, the DPPC, POPC, and POPG are at ratio of about (4-5):(2-3):(1-3). In another aspect, the DPPC, POPC, and POPG are at ratio of about (4-5):(2-3):(1-2). In another aspect, the DPPC, POPC, and POPG are at ratio of about (4-5):(3-4):(2-3). In another aspect, the DPPC, POPC, and POPG are at ratio of about (5-6):(2-4):(1-3). In another aspect, the DPPC, POPC, and POPG are at ratio of about (5-6):(3-4):(1-3). In another aspect, the DPPC, POPC, and POPG are at ratio of about (5-6):(3-4):(2-3). In another aspect, the DPPC, POPC, and POPG are at ratio of about (5-6):(2-3):(2-3). In another aspect, the DPPC, POPC, and POPG are at ratio of about (5-6):(2-3):(1-2).

In various embodiments described herein, the peptides described herein can be modified by the inclusion of one or more conservative amino acid substitutions. As is well known to those skilled in the art, altering any non-critical amino acid of a peptide by conservative substitution should not significantly alter the activity of that peptide because the side-chain of the replacement amino acid should be able to form similar bonds and contacts to the side chain of the amino acid, which has been replaced. Non-conservative substitutions may too be possible, provided that they do not substantially affect the binding activity of the peptide (i.e., collagen binding affinity).

The compositions can further include any one or more of a non-phospho surfactant. As used herein, the term "non-phospho surfactant" refers to surface active compounds that do not possess a phospho group (e.g., phosphate, phosphonate, etc.). Exemplary non-phospho surfactants include, without limitation, a free fatty acid, hexadecanol, or cholesterol.

Preferred free fatty acids include saturated and monounsaturated $C_{10}$ to $C_{24}$ hydrocarbons, more preferably $C_{12}$-$C_{20}$ hydrocarbons, most preferably $C_{14}$-$C_{18}$ hydrocarbons. Of these, saturated hydrocarbons are preferred.

The compositions of the present disclosure can be used for delivering additional pharmaceutical agents to a subject in need thereof. In one embodiment, the composition (or formulation) further includes a therapeutic agent. The therapeutic agent can be any agent that is shown, tested, or proposed to have therapeutic effects in a patient.

The compositions can be formulated as an inhalable composition that is delivered to a patient's conducting and central airways by inhalation. The composition preferably is formulated in an efficacious, safe, nonirritating, physiologically acceptable and compatible inhalable form. For aerosolization, composition can be delivered as a dry powder or as a solution. The composition can be formulated in a dry powder or solution for inhalation nebulized into an aerosol with a median mass aerodynamic diameter (MMAD) from about 0.5 μm, 1 μm, 2 μm, 3 μm, 4 μm, 5 μm, 6 μm, 7 μm, 8 μm, 9 μm, 10 μm, and within a range of any two of the foregoing values.

7. Methods of Administration

Aerosol delivery of the PGZ and B-YL formulation can be accomplished with a vibrating mesh nebulizer. However, both liquid and dry-powder nebulizers can also be used. The type of nebulizer can vary and the drug combination can be nebulized as a wet or dry preparation.

Nebulizers and pressurized metered-dose inhalers can be used to deliver aerosolized drugs. Nebulizers transform liquid formulations and suspensions into medical aerosol and are understood to include jet nebulizers, ultrasonic nebulizers and mesh nebulizers. Mesh nebulizers use lower-frequency waves and eliminate the heating issues that can denature proteins during aerosolization.

Mesh nebulizers typically force liquid medications through multiple apertures in a mesh or aperture plate to generate aerosol. Mesh nebulizers are advantageous because they provide consistent aerosol generation and a predominately fine-particle fraction reaching into the peripheral lung, low residual volume, and the ability to nebulize in low drug volumes. The size of the pore, the aerosol chamber, and the reservoir, as well as the output rate of mesh nebulizers, can be adjusted for different drugs in order to optimize aerosol drug delivery to patients.

Mesh nebulizers can be classified as active mesh nebulizers and passive mesh nebulizers. Active mesh nebulizers use a piezo element that contracts and expands on application of an electric current and vibrates a precisely drilled mesh in contact with the medication to generate aerosol. One suitable mesh nebulizer for the compositions described herein is the Aeroneb (Aerogen, Galway, Ireland) nebulizers which can be used for both spontaneously breathing and ventilator-dependent patients.

The aerosolized composition can be administered using either a mouthpiece or a face mask, with a face mask being suitable for infants, small children, and patients with cognitive problems. The aerosolized composition can have a MMAD of 0.5 µm, 1 µm, 1.5 µm, 2 µm, 2.5 µm, 3 µm, 3.5 µm, 4 µm, 4.5 µm, 5 µm, 5.5 µm, 6 µm, 6.5 µm, 7 µm, 7.5 µm, 8 µm, 8.5 µm, 9 µm, 9.5 µm, or 10 µm. The MMAD may also be within a range between any two of the foregoing values.

The compositions of the present disclosure can be used to treat lung tissue that is characterized by deficiency and/or dysfunction of endogenous surfactant (i.e., "surfactant deficient or dysfunctional lung tissue"), such as RDS, and also to reduce or to prevent the adverse symptoms or disorders associated with hyperoxia, including but not limited to chronic lung disease, such as BPD, and lung immaturity.

In certain embodiments, the deficiency of endogenous surfactant can be a reduced amount or an abnormal composition of endogenous surfactant (i.e., not enough is present or the composition thereof is ineffective) or the complete absence of an endogenous surfactant, and the surfactant dysfunction can be a reduced activity of endogenous surfactant either present intrinsically or acquired during disease. Thus, the term "treatment" of surfactant deficient and/or dysfunctional lung tissue is meant to include a prophylactic or therapeutic regimen that can inhibit onset of RDS, for example, in premature infants, chronic lung disease, such as BPD, or the onset of acute lung injury (ALI) or the acute respiratory distress syndrome (ARDS) in patients of any age, or otherwise improve respiratory function, lung pressure-volume mechanics, or clinical outcome when administered for therapeutic treatment of a pre-existing conditions such as acute or neonatal RDS, or ALI, or ARDS. As used herein, "treatment" contemplates complete therapeutic resolution of a condition as well as improving conditions to minimize symptoms of RDS or ALI/ARDS.

The treatments in accordance with this aspect of the disclosure involve administering a composition of the present disclosure to a patient having lung tissue characterized by endogenous surfactant deficiency and/or dysfunction, where the administering is carried out under conditions effective to coat alveolar surfaces of the affected lung tissue with the composition, thereby treating the surfactant deficient and/or dysfunctional lung tissue. The patient may also have a lung condition or disorder associated with hyperoxia.

The patient to be treated can be a premature infant who is characterized by either the complete absence of endogenous surfactant or an ineffective amount of endogenous surfactant or an acquired dysfunction of endogenous surfactant during the clinical course as well as a hyperoxia-induced lung disorder. In either case, the composition of the present disclosure can be administered in a manner effective to prevent onset of neonatal respiratory distress syndrome (when administered immediately following intubation), or reduce the severity of respiratory deficit in acute respiratory distress syndrome and/or acute lung injury (when administered some time after initial intubation), as well as reduce the likelihood or prevent the progression of BPD. Administration of the composition is preferably via aspiration, airway instillation, aerosolization, or nebulization. Administration of the composition can be administered periodically over a course of treatment to maintain lung function in the infant, preferably until the infant's lung tissue is capable of producing sufficient endogenous surfactant to maintain lung function in the absence of intervention. In one embodiment, provided is a method of treating surfactant deficiency or dysfunction in a patient in need thereof, comprising administration to the patient a PPAR gamma agonist; one or more surfactant peptides; and one or more phospholipids. In one embodiment, the PPAR gamma agonist, the one or more surfactant peptides, and the one or more phospholipids are administered concurrently or sequentially.

The patient to be treated can also be an individual that otherwise should be able to produce active endogenous surfactant, but due to lung tissue disease or disorder either has deficient levels of endogenous surfactant or existing endogenous surfactant has become inhibited or inactivated in activity. In addition, the patient can be an individual has any one or more of the following conditions: lung immaturity, fluid-filled lungs, lung injury resulting from ventilation treatment, including mechanical or continuous positive airway pressure (CPAP) ventilators, hyperoxia-induced lung injury, acute lung injury due to infection or any other cause, respiratory distress syndrome (RDS), chronic lung injury, chronic bronchopulmonary dysplasia (BPD), downregulation of pulmonary mesenchymal PPAR gamma, upregulation of myogenic signaling pathways, transdifferentiation of lipid-rich alveolar interstitial fibroblasts to myofibroblasts, asthma, nicotine exposure-induced lung injuries, nicotine exposure-induced asthma, insufficient alveolar development of the lungs, and insufficient vascular development of the lungs.

In this embodiment, the patient is a full-term infant, child, or adult. Endogenous surfactant production can be deficient due to acute lung injury caused by pulmonary disease or infection, systemic disease or infection, or other direct or indirect causes such as burns, trauma, shock, aspiration syndromes, drug overdose, multiple blood transfusions, pancreatitis, or other known causes of ALI/ARDS. In either acquired surfactant deficiency or dysfunction, the surfactant composition of the present disclosure can be administered in a manner effective to reduce the severity of respiratory deficit in acute respiratory distress syndrome and/or acute lung injury. The composition may also be administered prophylactically to such patients to prevent the onset of ALI/ARDS. Administration of the composition is preferably via aspiration, airway instillation, aerosolization, or nebulization. Administration of the surfactant can be administered periodically over a course of treatment to maintain lung function in the individual being treated.

Another aspect of the present disclosure relates to a method of delivering a therapeutic agent (examples provided above). By virtue of the surface activity of the compositions of the present disclosure, it is believed that the compositions of the present disclosure will readily form liposomal vesicles that can be used to deliver therapeutic agents to a patient. Thus, this method of the present disclosure includes introducing a therapeutic agent into a composition of the present disclosure under conditions effective to encapsulate the therapeutic agent in liposomal vesicles, and then administering the composition to a subject under conditions effective to deliver the therapeutic agent to a target tissue. The administration can be any suitable approach for delivery of the therapeutic agent to a target tissue, but preferably aspiration, airway instillation, aerosolization, nebulization, intranasal instillation, oral or oropharyngeal instillation, intraperitoneal injection, or intravascular injection. The target tissue can be lung tissue or a systemic tissue. The agent or agents to be delivered can be any pharmaceutical or therapeutic agent including those listed above as well as a systemic or local anti-tumor agent, a systemic or local gene therapy agent, a systemic or local anti-inflammatory agent or antioxidant, a systemic or local vasoactive agent, a systemic or local agent modifying immune responses, blood cells, or host-defense.

Devices useful for administering the surfactants are also disclosed, such as for nasal, oropharyngeal or intratracheal delivery. For instance, U.S. Pub. No. 2014/0216449 describes devices for surfactant administration and ventilation of low birth weight infants. The entire contents of U.S. Pub. 2014/0216449 are incorporated herein by reference.

EXAMPLES

Example 1. Formulations of PGZ and B-YL Surfactant

In a first vessel, 15.7 mg pioglitazone (PGZ) and 3.92 mL of ethanol were combined to produce a composition of 4 mg PGZ/ml. In a second vessel, 1.05 mg B-YL (SEQ ID NO: 15) (3%) and 35 mg of DPPC:POPC:POPG in a 5:3:2 wt:wt:wt ratio was combined to form a B-YL composition and heated to about 50° C.

The PGZ-ethanol composition was then added to the heated B-YL composition and the resulting mixture was evaporated under reduced pressure for 30 minutes for about 50° C. in a rotary evaporator (rotovap) to ensure incorporation of the PGZ in the B-YL composition. The resulting mixture of PGZ and B-YL composition was then freeze-dried overnight to remove ethanol. The freeze-dried product was then hydrated to the original volume with Milli-Q water and dispersed by a rotovap for about 50° C. for 1 hour before storing overnight at 5° C.

Example 2. Treatment with Synthetic Surfactant B-YL and PGZ Increases Expression of Markers for Lung Maturation In this example, the expression of various markers for lung maturation by embryonic day 19 fetal rat lung explants treated with mixtures of PGZ and B-YL synthetic surfactant were quantified by Western blot.

Embryonic day 19 fetal rat lung explants were cultured for 24 hours under the following conditions: (1) control conditions (i.e., no exposure to B-YL and no PGZ), (2) treated with 100 mg/kg per body weight of B-YL alone, or (3) treated a combination of PGZ and B-YL at 0.5, 1 and 2 mg/kg per body weight of PGZ and 100 mg/kg per body weight of B-YL.

Fetal rat explants treated with a combination of PGZ and the synthetic surfactant B-YL demonstrated increases in the expression of markers for lung maturation at the three different concentrations of PGZ. FIGS. 1A-1C demonstrate the increased expression of PPARγ (FIG. 1A), surfactant protein SP-C (FIG. 1B), and cholinephosphate cytidylyl-transferase (CCT)-α protein levels (FIG. 1C), as demonstrated by Western blot analysis. Additionally, FIG. 1D demonstrates a significant increase in [3H]choline incorporation into disaturated phosphatidylcholine, p<0.05 vs. control, n=3.

Example 3. Concomitant Administration of Nebulized Synthetic Surfactant B-YL and PGZ Protects Against Neonatal Lung Injury and Bronchopulmonary Dysplasia Postnatal day 1 Sprague Dawley rat pups were exposed to hyperoxia (95% 02) under the following conditions: (1) control group (no PGZ or B-YL), (2) administration of nebulized PGZ only, and (3) concomitant administration of nebulized PGZ and B-YL.

At the end of the experimental period, markers for lung injury such as epithelial and mesenchymal markers of alveolar differentiation (FIGS. 2A-2F), apoptosis marker BcL2/Bax and lung inflammatory markers IL-6 and inferon γ (FIGS. 3A-3C) and hyperoxia-induced activation of TGF-β and Wnt signaling pathways (FIGS. 4A-4B) were determined.

Figures 2D, 2E, 2F:
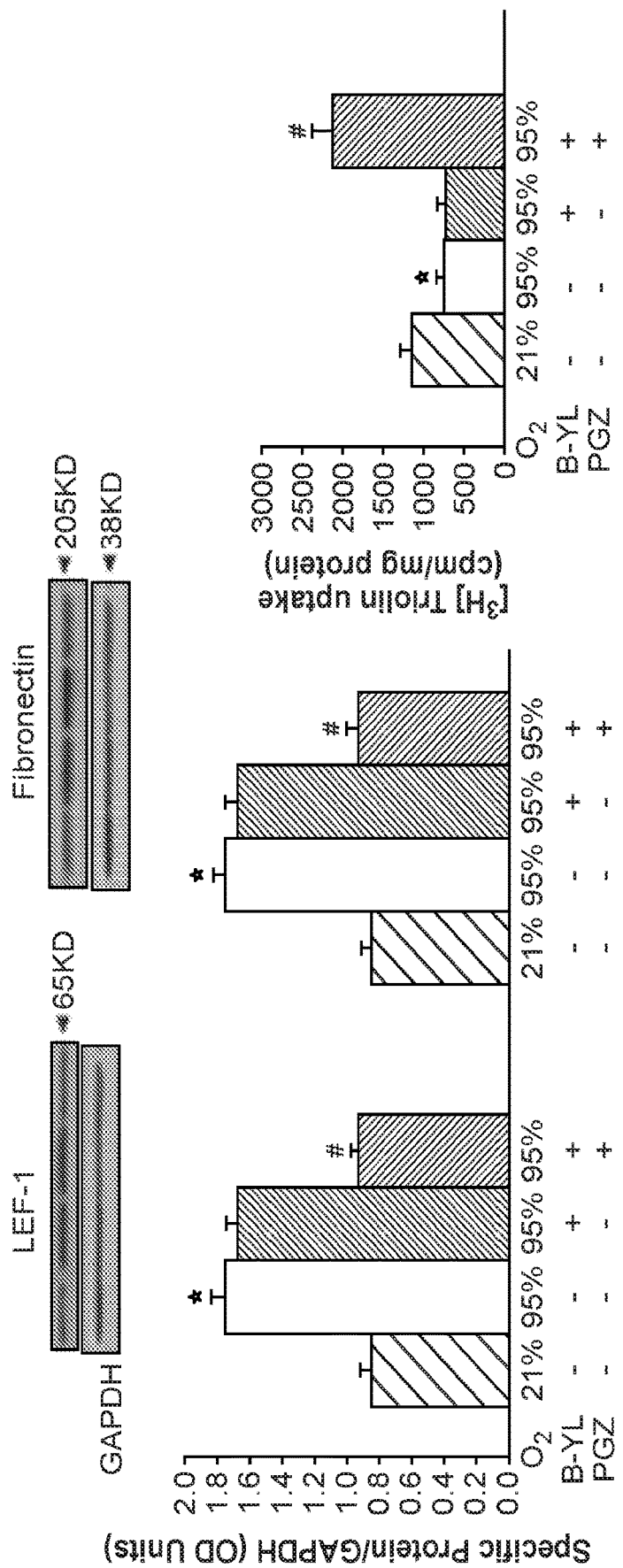

Concomitant administration of nebulized PGZ and B-YL was demonstrated to block hyperoxia-induced neonatal lung injury. The rat pups were exposed to hyperoxia for 72 hours, both in the presence and absence of B-YL surfactant and also in the presence of the combination of PGZ and B-YL surfactant. Hyperoxia-induced decrease in PPARγ (FIG. 2A), SP-C surfactant protein (FIG. 2B), CCT-α (FIG. 2C) were observed and increases in LEF-1 (FIG. 2D), fibronectin (FIG. 2E) blocked by concomitant administration of PGZ and B-YL. Similarly, hyperoxia-induced decrease in triolein uptake was also blocked by concomitant administration of PGZ and B-YL (FIG. 2F). Concomitant administration of nebulized PGZ and B-YL also resulted in hyperoxia-induced alterations in the apoptosis marker BcL2/Bax ratio (FIG. 3A) and blocking of inflammatory markers IL-6 (FIG. 3B) and IF-γ (FIG. 3C).

Postnatal day 1 Sprague Dawley rat pups were also exposed to hyperoxia with and without the concomitant administration of nebulized PGZ and B-YL (q 24 h×3) for 72 hours. Hyperoxia-induced activation in TGF-0, as determined by ALK5 protein levels, red staining, and Wnt (as determined by β-catenin protein levels, green staining) signaling was blocked by concomitant administration of PGZ and B-YL. FIGS. 4A-4C provide representative immunostaining pictures.

Figure 5:
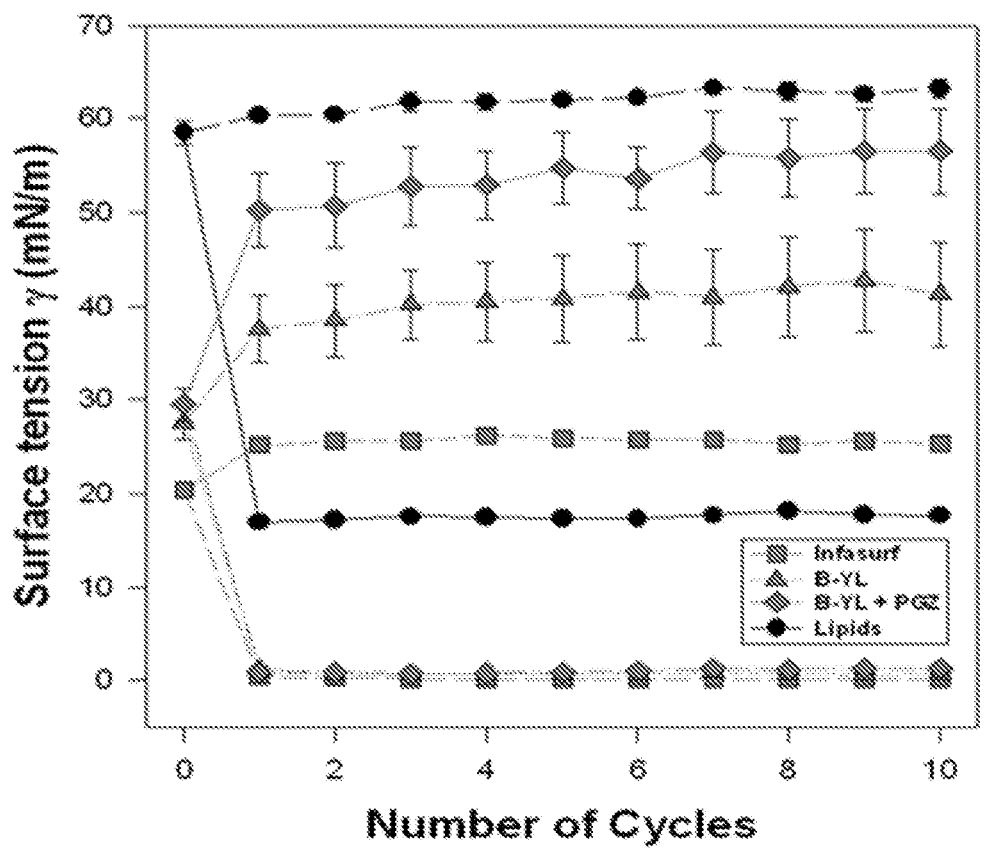
FIG. 5 is a graph comparing the surface activity of Infasurf® (positive control), B-YL surfactant, the combination of B-YL, phospholipids, and PGZ, at two different concentrations of B-YL (50 and 100 mg/kg of B-YL and lipids in combination with 1 mg/kg PGZ), and the phosophlipids alone (DPPC:POPC:POPG at a 5:3:2 wt:wt:wt) (negative control).

Example 4. Concomitant Administration of Nebulized Synthetic Surfactant B-YL and PGZ Protects Against Neonatal Lung Injury and Bronchopulmonary Dysplasia Surface activity of the B-YL surfactant was measured using captive bubble surfactometry (CBS) in the presence and absence of PGZ (dosing target for B-YL surfactant was 50 and 100 mg/kg and of PGZ 1 mg/kg) and compared with Infasurf®, a clinical surfactant, as a positive control and lipids alone (DPPC:POPC:POPG at a 5:3:2 wt:wt:wt) as a negative control. Minimum surface tension values of B-YL surfactant with and without PGZ were similar to those of Infrasurf® as demonstrated in FIG. 5. Aerosolization of B-YL surfactant with a vibrating mesh nebulizer (Aeroneb Pro® nebulizer, Aerogen Inc., Mountain View, Calif.) delivered particles with a median mass aerodynamic diameter (MMAD) between 1 and 3 µm.

Figure 6:
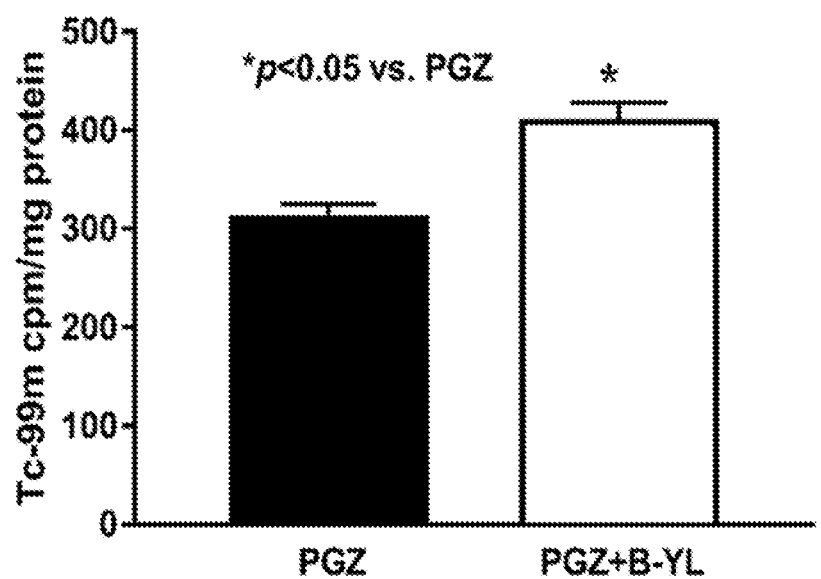
FIG. 6 is a bar graph showing that addition of B-YL surfactant to PGZ improved nebulized PGZ delivery to lungs.

Example 5. Addition of B-YL Surfactant to PGZ Improves Nebulized PGZ Delivery to Lungs The following is to study the effect of radio-labeled B-YL on nebulized PGZ delivery to Lungs. Tc-99m DTPA (diethylene-triamine-pentaacetate) was used as a radioactive agent to label B-YL (100 MBq Tc-99m-DTPA/100 mg of B-YL). Delivery of radio-labeled B-YL to lungs nebulized over 30 minutes with or without added PGZ was determined. The results demonstrated 30% higher delivery of PGZ to both lungs when nebulized as PGZ+B-YL vs PGZ alone (p<0.05) as demonstrated in FIG. 6. The results suggested that the combinatorial approach augments PGZ delivery and potentially its lung maturational and injury-protectant effects.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. An aerosol delivery device comprising an inhaler or nebulizer loaded with:
   a PPAR (peroxisome proliferator-activated receptor) gamma agonist;
   one or more surfactant peptides; and
   one or more phospholipids,
   wherein at least one of the one or more surfactant peptides comprises:
   (i) a first fragment comprising the amino acid sequence of XWLXRALIKRIQAZI (SEQ ID NO: 1) or a first amino acid sequence having at least 90% sequence identity to SEQ ID NO: 1 and (ii) a second fragment comprising the amino acid sequence of RZLPQLVXRLVLRXS (SEQ ID NO: 2) or a second amino acid sequence having at least 90% sequence identity to SEQ ID NO: 2, wherein (a) X is any amino acid but at least one amino acid at the X positions is tyrosine, and (b) Z is any amino acid but not methionine.

2. The aerosol delivery device of claim 1, wherein the PPAR gamma agonist is a thiozolidinedione (TZD).

3. The aerosol delivery device of claim 2, wherein the TZD is selected from the group consisting of: a rosiglitazone, a troglitazone, a farglitazar, a phenylacetic acid, a GW590735, a GW677954, a GW1929, an 52648, an Avandia, an Avandamet, a ciglitazone, a pioglitazone, an adaglitazone, a 15 deoxy prostaglandin J2, a 15-deoxy-delta12,14 PGD2, GW-9662, a MCC-555, a LG100754, an nTZDpa, and a Telmisartan.

4. The aerosol delivery device of 3, wherein the TZD is a pioglitazone.

5. The aerosol delivery device of 1, wherein the PPAR gamma agonist is an endogenous natural compound with PPAR gamma activity or a metabolite thereof.

6. The aerosol delivery device of claim 5, wherein the surfactant peptide further comprises (iii) a turn between the first fragment and the second fragment.

7. The aerosol delivery device of claim 6, wherein the turn comprises PKGG (SEQ ID NO: 3).

8. The aerosol delivery device of claim 6, wherein the turn can form a salt bridge between amino acids within the turn or between the turn and the first or second fragment.

9. The aerosol delivery device of claim 6, wherein the turn comprises DATK (SEQ ID NO: 4).

10. The aerosol delivery device of claim 5, wherein the surfactant peptide further comprises an insertion sequence at the N-terminal end of the first fragment.

11. The aerosol delivery device of claim 10, wherein the insertion sequence comprises FPIPLPY (SEQ ID NO: 5).

12. The aerosol delivery device of claim 5, wherein none amino acid at the X positions of the surfactant peptide is cysteine.

13. The aerosol delivery device of claim 12, wherein the amino acid at each X position of the surfactant peptide is selected from the group consisting of Y, L, A, and F.

14. The aerosol delivery device of claim 1, wherein the one or more phospholipid is selected from the group consisting of dipalmitoylphosphatidylcholine (DPPC), palmitoyloleoylphosphatidylcholine (POPC), phosphatidylglycerol (PG), palmitoyloleoylphosphatidylglycerol (POPG), cholesterol (Chol), 1,2-Dioleoyl-sn-glycero-3-phosphocholine (DOPC), 1-Palmitoyl-2-oleoyl-sn-glycero-3-phosphoethanolamine (POPE), 1-palmitoyl-2-oleoylsn-glycero phosphocholine (POPS), 1,2-Distearoyl-sn-glycero-3-phosphocholine (DSPC), 1,2-Dipalmitoyl-sn-glycero-3-phosphoethanolamine (DPPE), 1,2-dipalmitoyl-sn-glycero-3-phosphoglycerol (DPPG), DEPN-8, PG-1 and combinations thereof.

15. The aerosol delivery device of claim 14, wherein the one or more phospholipid comprises DPPC, POPC, and POPG.

16. The aerosol delivery device of claim 15, wherein the DPPC, POPC, and POPG are at ratio of about (4-6):(2-4): (1-3).

17. A method of treating surfactant deficiency or dysfunction in a patient in need thereof, comprising aerosol administration to the patient the PPAR gamma agonist; the one or more surfactant peptides; and the one or more phospholipids loaded in the inhaler or nebulizer of claim 1.

18. The method of claim 17, wherein the surfactant deficiency or dysfunction comprises a respiratory distress syndrome in an infant or a respiratory distress syndrome secondary to surfactant deficiency or lung immaturity in a premature or near-term infant.

\* \* \* \* \*